US00PP21933P2

(12) United States Plant Patent
Egger

(10) Patent No.: US PP21,933 P2
(45) Date of Patent: May 24, 2011

(54) ***TIARELLA* PLANT NAMED 'HAPPY TRAILS'**

(50) Latin Name: ***Tiarella* spp.**
Varietal Denomination: Happy Trails

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 19 days.

(21) Appl. No.: 12/653,642

(22) Filed: Dec. 14, 2009

(51) Int. Cl.
*A01H 5/00* (2006.01)

(52) U.S. Cl. ..... Plt./486

(58) Field of Classification Search ..... Plt./486
See application file for complete search history.

*Primary Examiner* — Wendy Haas
(74) *Attorney, Agent, or Firm* — Klarquist Sparkman, LLP

(57) ABSTRACT

A new and distinct cultivar of *Tiarella* plant characterized by small palmately-lobed leaves, with the terminal lobe the longest, an excellent trailing habit, distinct, dark brown markings following the veins, and excellent vigor.

1 Drawing Sheet

Botanical denomination: *Tiarella* spp.
Variety designation: 'Happy Trails'.
Cross Reference to sibling: *Tiarella* 'Cascade Creeper' (U.S. Plant patent application Ser. No. 12/653,543).

BACKGROUND OF THE INVENTION

The present invention relates to a new and distinct cultivar of a hardy herbaceous perennial of the genus *Tiarella*, and known by the cultivar name 'Happy Trails'. The genus *Tiarella* is a member of the family Saxifragaceae.

The new cultivar originated from a planned breeding program as a cross between *Tiarella* 27-04, a proprietary, unreleased trailing *Tiarella* as the seed parent and massed proprietary trailing *Tiarella* as the pollen parent. The exact pollen parent is unknown. Compared to the seed parent, *Tiarella* 27-04, the new cultivar is more trailing and better marked. Compared to other trailing *Tiarella* on the market the new cultivar has a larger, darker central pattern.

SUMMARY OF THE INVENTION

This plant is characterized by the following:

1. small palmately-lobed leaves, with the terminal lobe the longest,
2. an excellent trailing habit,
3. distinct, dark brown markings following the veins,
4. and excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows *Tiarella* 'Happy Trails' grown outside in the garden in October in Canby, Oreg.

FIG. 2 shows a close up of the foliage and flowers in the spring from plants grown indoors.

DETAILED PLANT DESCRIPTION

The following is a detailed description of the new *Tiarella* cultivar based on observations of two, one-year-old plants grown together in a 10" hanging basket in the greenhouse in June in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart, $5^{th}$ edition.

Plant:
- *Type.*—Herbaceous perennial.
- *Hardiness.*—USDA Zones 4 to 9.
- *Form.*—Trailing.
- *Size.*—92 cm wide and 12 cm high from the soil to the top of the foliage.
- *Vigor.*—Excellent.
- *Roots.*—Fibrous, freely branching, fine, and white in color; roots develop easily from stem cuttings.

Stem:
- *Type.*—Decumbent with adventitious roots at the nodes.
- *Size.*—Grows to 3 mm wide and 40 cm long.
- *Surface.*—Pubescent.
- *Internodes.*—3 cm to 4 cm long.
- *Color.*—Between Greyed Purple 187B and Brown 200B.

Foliage:
- *Type.*—Simple.
- *Arrangement.*—Rosette and alternate.
- *Shape.*—Ovate overall.
- *Lobing.*—Variable, 5 to 7 main lobes, the terminal lobe is the longest, each main lobe with 0 to 2 lateral lobes.
- *Margins.*—Entire to broadly crenate.
- *Venation.*—Palmate.
- *Apex.*—Mucronulate.
- *Base.*—Cordate, usually overlapping.
- *Blade.*—Grows to 7 mm long and 6 mm wide.
- *Surface.*—Hispid top and bottom, matte.

*Petiole description.*—3 to 5.5 cm, hirsute, between Greyed Purple 187B and Brown 200B in light and Yellow Green 146C in shade.

*Leaf color.*—Topside, Green 137A with a dark pattern along the veins, Greyed Purple N186A, bottom side Yellow Green 147B.

Inflorescence:

*Type.*—Raceme.

*Flower number.*—30 to 40 per raceme.

*Size of inflorescences.*—Grows to 13.5 cm long and 2.5 cm wide.

*Number of inflorescences.*—17 in spring.

*Bloom period.*—April to mid June in Canby, Oreg.

*Peduncle.*—Usually unbranched, grows to 28 cm long and 2.5 mm wide at the base, hispid, between Greyed Purple 187B and Brown 200B.

*Pedicel.*—5 mm long, hispid, Purple N77D.

*Lastingness.*—A raceme blooms for about 3 weeks.

Flower Bud:

*Size.*—4 mm deep and 2 mm wide.

*Description.*—Ovoid, down facing until open.

*Surface.*—Glandular.

*Color.*—Purple 75C.

Flower:

*Type.*—Perfect, actinomorphic, sepals petaloid.

*Shape.*—Rotate.

*Flower size.*—8 mm wide and 6 mm deep including stamens and pistil.

*Corolla.*—5 petals, each 4 mm long and 1 mm wide, lanceolate with a clawed base, entire, acuminate, glabrous on both sides, White NN155D inside and outside.

*Calyx.*—5 mm wide, 5 sepals, backs glandular, inside glabrous, petaloid, parted almost to the base, lobes obovate, obtuse, entire, 2.5 mm long and 1.2 mm wide, White N155A inside and out.

*Stamens.*—10, conspicuously exerted; filaments 4 mm long, White NN155D; anthers undehisced Orange 26C; pollen Yellow 11C.

*Pistil.*—1, White 155C, 6 mm long, ovary 2 mm long, glandular.

*Fragrance.*—None.

Fruit and seed: 6 mm long and 2.5 mm wide, Yellow Green 146C with little seed set; seed Brown 200A, oval, 1.5 mm long.

Pest and disease resistance: This new hybrid shows good mildew tolerance, the main problem for *Tiarella*. No major pest problems. It is susceptible to root weevils, like all *Tiarella*.

I claim:

1. A new and distinct cultivar of *Tiarella* plant herein illustrated and described.

* * * * *

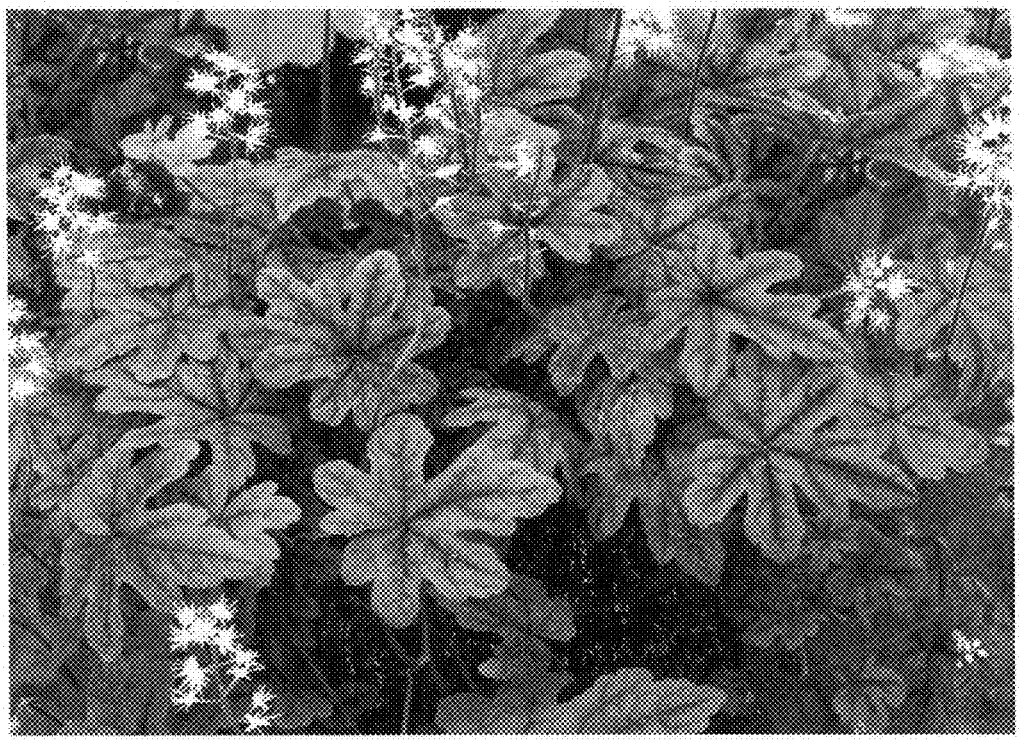

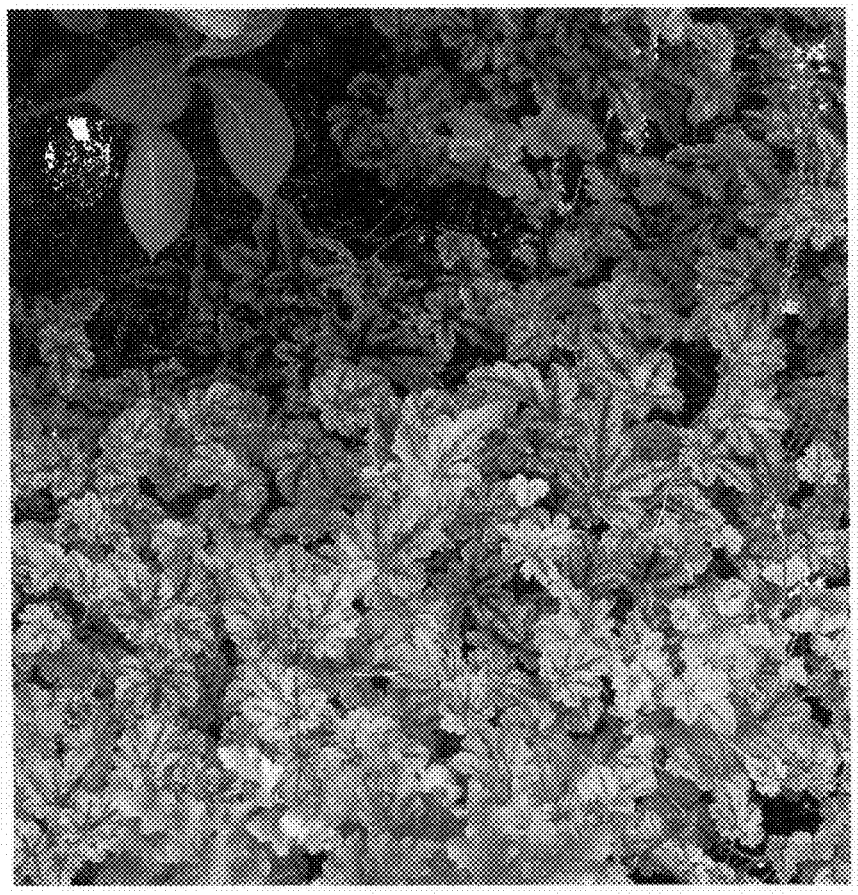
Figure 1 above, Figure 2 below.